United States Patent [19]
Jori

[11] Patent Number: 6,107,326

[45] Date of Patent: Aug. 22, 2000

[54] PORPHYCENES FOR TREATMENT OF MICROBIAL POPULATIONS

[75] Inventor: Giulio Jori, Padua, Italy

[73] Assignee: Cytopharm, Inc., Menlo Park, Calif.

[21] Appl. No.: 09/289,637

[22] Filed: Apr. 12, 1999

[51] Int. Cl.$^7$ .......................... A61K 31/40; C07D 487/22
[52] U.S. Cl. .............................. 514/410; 514/2; 540/145
[58] Field of Search ............................ 540/145; 514/410, 514/2

[56] References Cited

U.S. PATENT DOCUMENTS

| | | | |
|---|---|---|---|
| 4,913,907 | 4/1990 | Jori et al. | 424/450 |
| 5,015,478 | 5/1991 | Jori et al. | 424/450 |
| 5,132,101 | 7/1992 | Vogel et al. | 514/410 |
| 5,179,120 | 1/1993 | Vogel et al. | 514/410 |
| 5,244,671 | 9/1993 | Vogel et al. | 424/450 |
| 5,262,401 | 11/1993 | Vogel et al. | 514/32 |
| 5,409,900 | 4/1995 | Vogel et al. | 514/17 |
| 5,610,175 | 3/1997 | Vogel et al. | 514/410 |
| 5,637,608 | 6/1997 | Vogel et al. | 514/422 |
| 5,756,724 | 5/1998 | Vogel et al. | 540/145 |

OTHER PUBLICATIONS

*Journal of Antimicrobial Chemotherapy* (1998) 42. 13–28, Mark Wainwright "Photodynamic antimicrobial chemotherapy (PACT)".

Z. Malik, et al., Journal of Photochemistry and Photobiology. B: Biology, vol. 5, pp. 281–293, "New Trends in Photobiology (Invited Review) Bactericidal Effects of Photoactivated Porphyrins—An Alternative Approach to Antimicrobial Drugs", 1990.

Z. Malik, et al., Journal of Photochemistry and Photobiology. B: Biology, vol. 14, pp. 262–266, "Photodynamic Inactivation of Gram–Negative Bacteria: Problems and Possible Solutions", 1992.

G. Valduga, et al., Journal of Photochemistry and Photobiology. B: Biology, vol. 21, pp. 81–86, "Effect of Extracellularly Generated Singlet Oxygen on Gram–Positive and Gram–Negative Bacteria", 1993.

B. Ehrenberg, et al., Photochemistry and Photobiology, vol. 41, No. 4, pp. 429–435, "Fluorescence Spectral Changes of Hematoporphyrin Derivative Upon Binding to Lipid Vesicles, *Staphylococcus aureus* and *Escherichia coli* Cells", 1985.

G. Valduga, et al., Biochemical and Biophysical Research Communications, vol. 256, pp. 84–88, "Photosensitization of Wild and Mutant Strains of *Escherichia coli* by Meso–Tetra (N–Methyl–4–Pyridyl)Porphine", 1999.

A. Minnock, et al., Journal of Photochemistry and Photobiology. B: Biology, vol. 32, pp. 159–164, "Photoinactivation of Bacteria. Use of a Cationic Water–Soluble Zinc Phthalocyanine to Photoinactivate Both Gram–Negative and Gram–Positive Bacteria", 1996.

*Primary Examiner*—Richard L. Raymond
*Assistant Examiner*—Pavanaram K Sripada
*Attorney, Agent, or Firm*—Oblon, Spivak, McClelland, Maier & Neustadt, P.C.

[57] ABSTRACT

Cationic porphycenes are conjugated, through a carboxylic-acid bearing moiety, with polylysine through an amide linkage. The novel porphycenes are effective in treating microbial populations in vitro or in vivo and topically as well as for sterilizing articles.

19 Claims, 11 Drawing Sheets

FIG. 9

COLONY FORMING UNITS (log CFU/ml) AND PERCENT SURVIVAL (%) OF S.aureus, E.coli, C.albicans AND A.laidlawii INCUBATED FOR 30min IN THE DARK WITH 1$\mu$M POLY-LYSINE-BOHTMPn CONJUGATE AND IRRADIATED WITH WHITE LIGHT AT A FLUENCE RATE OF 150mW/cm$^2$.

| IRRADIATION TIME(min) | log CFU/ml(%) | | | |
| --- | --- | --- | --- | --- |
| | S.aureus | E.coli | C.albicans | A.laidlawii |
| control | 8.99 (100) | 8.55 (100) | 7.30 (100) | 7.18 (100) |
| 0 | 8.36 (23.5) | 8.41 (72) | 7.11 (65) | – |
| 1 | – | – | – | 3.38 (0.015) |
| 5 | 7.30 (2.0) | 6.48 (0.83) | 6.61 (21) | 2.40 (0.0016) |
| 15 | 5.44 (0.03) | 5.28 (0.05) | 5.56 (1.8) | – |
| 30 | 4.98 (0.01) | 5.30 (0.05) | 4.36 (0.1) | – |

FIG. 10

SURVIVAL (%) OF NORMAL HUMAN FIBROBLASTS AND B78H1 MELANOMA CELLS AFTER 30min INCUBATION IN THE DARK WITH VARIOUS CONCENTRATIONS OF THE POLY-LYSINE-BOHTMPn CONJUGATE.

| BOHTMPn $\mu M$ | CELL SURVIVAL (%) | |
| --- | --- | --- |
| | FIBROBLASTS | B78H1 |
| 0.25 | 75 | 78 |
| 0.50 | 60 | 64 |
| 1.00 | 54 | 50 |

FIG. 11

SURVIVAL (%) OF NORMAL HUMAN FIBROBLASTS AFTER 30 min. INCUBATION WITH DIFFERENT POLY-LYSINE CONCENTRATIONS.

| POLY-LYSINE CONCENTRATIONS ($\mu$M) | CELL SURVIVAL (%) | |
| --- | --- | --- |
| | POLY-LYS MW 1000-4000 | POLY-LYS MW 15000-30000 |
| 0.25 | – | 57 |
| 1.00 | 84 | 0-15 |
| 5.00 | 100 | – |

PORPHYCENES FOR TREATMENT OF MICROBIAL POPULATIONS

BACKGROUND OF THE INVENTION

1. Field of the Invention

This invention pertains to novel porphycene compounds having effectiveness in the treatment and eradication of microbial populations, and other anti-microbial properties, as well as compositions comprising the same, and methods of using these porphycenes to treat microbial infection.

2. Discussion of the Background

During the past three decades an accelerating volume of research has been conducted and published concerning the use of photodynamic therapy (PDT) in treatment of hyperproliferative disease. Only one product had received U.S. regulatory approval prior to December, 1998, and this, a first generation dye mixture of uncertain composition, possesses acknowledged deficiencies in clinical applications for limited approved uses in treatment of various cancers. Since 1970, numerous photoactivatable compounds have been synthesized and studied in vitro and in vivo in the search for superior, second generation dyes. Much of this work has centered upon the porphyrinoid dyes containing a tetrapyrrolic macrocycle as the light energy absorbing moiety. One unique ring system is exemplified by the porphycenes, also cyclic tetrapyrroles, though isomeric with the naturally occurring porphyrin ring system. A selective summary of relevant patent and scientific literature references to PDT research and clinical applications is covered, for example, in U.S. Pat. No. 5,610,175, Vogel et. al., where each references cited in turn offers many more references.

Phase II or Phase III clinical studies are being conducted with a variety of photosensitisers or precursors including a porphycene (Cytopharm), an etiopurpurin (Miravant Technologies), a benzoporphyrin (QLT Phototherapeutics), δ-aminolevulinic acid (DUSA), chlorins (Nippon Petrochemical and Scotia), and an expanded porphyrin system (Pharmacyclics), among others. δ-Aminolevulinic acid (ALA) is not a photoactivatable dye itself but undergoes endogenous in vivo metabolism to the active molecule protoporphyrin IX (Pp=IX). All of these photosensitizing dyes under clinical development, except the porphycene and ALA, appear to be administered systemically, based on the published literature. Thus, of the tetrapyrroles, only the porphycenes appear to lend themselves to topical application, which is a favored route of administration for several medical treatments, as exemplified by dermatological diseases.

For PDT treatment of microbial infections, as in periodontal disease, and for wound sterilization in hospital or field conditions, human or animal, a desirable photoactivatable agent should possess preferably the following properties:

- Application as a topical formulation
- Ability to penetrate or bind to bacterial cell walls
- Non-toxic to host cells
- Rapid metabolism if escape to vascular system occurs
- Efficacy against fungal organisms and yeasts
- Efficacy against both Gram positive and Gram negative bacteria
- Efficacy in destruction of antibiotic-resistant bacteria
- Excellent kill of a wide range of microorganisms
- Fast-acting, allowing light radiation within minutes of application
- Efficacy at low concentration of dye
- Efficacy with lower light dose than will destroy host cells ALA requires several hours to undergo metabolism to Pp-IX and is therefore unsuitable for PDT when only a brief period can elapse between dye application and radiation with light.

The early porphycenes synthesized by Vogel et al. (*Angew. Chein. Int. Ed. Eng.*, 26, 928–931 (1987)) carried an alkyl substituent on each of the four pyrrole rings. In vivo assays revealed that these lipophilic molecules generally needed 12–48 hours to attain the optimal concentration in tumor tissue with highest selectivity for tumor versus non-tumor tissue (Guardiano et al. *Cancer Letters*, 44, 1–6 (1989)). Conversely, porphycenes synthesized later bearing an alkoxyalkyl substituent on each pyrrole ring were shown to penetrate hyperproliferative cells extremely rapidly, allowing tumor destruction by PDT procedures with light radiation just minutes after dye administration. (Richert et al., *J. Med. Chem*, 37, 2797 (1994) and Richert et al., *Photodynamic Therapy and Biomedical Lasers, Excerpta Medica*, 1011, 702, (1992)). Subsequently, independent work confirmed this attractive property conferred by alkoxyalkyl substituents in other porphyrin molecules (Bellnier et al., *J. Photocheni. Photobiol. B Biol*, 20, 55–61 (1993)). Thus, a class of porphycenes is available which offers both fast-action and permits topical application.

For anti-microbial activity the selected photoactivatable agent needs to penetrate or bind to the bacterial cell wall. There is work by Malik et al,. (*J. Photochem. Photobiol., B. Biol.*, 5, 281–293 (1990)), by Bertoloni et al.,(*FEMS Microbiological Letters*, 7, 149–156 (1990)) and by Nitzam et al.,(*Photochem. Photobiol*., 55, 89–96 (1992)) showing that neutral or anionic porphyrinoids are unable to induce the photinactivation of Gram (−) bacteria unless some agent permeabilizing their outer wall is previously added. Malik et al also showed that a cationic peptide (polymixin B) destabilizes the outer wall by replacing $Ca^{2+}$ ions so that the permeability of the outer wall is increased and the photosensitizer can penetrate to reach the cytoplasmic membrane. Hitherto no cationic porphyrinoid photosensitizers have been synthesized which meet all the criteria listed above to qualify as suitable photoactivatable dyes for PDT of microbial infections.

Attempts to inactivate Gram negative bacteria by exposure to light plus other porphyrinoid photosensitizers, including Photofrin®, verteporfin (BPD), temporfin (m-THPC), phthalocyanines, chlorins, etiopurpurins, etc. have proven unsuccessful.

In spite of the progress made in the area of photactivated anti-microbial agents, improvements in such agents are sought.

SUMMARY OF THE INVENTION

One embodiment of the present invention is a porphycene compound conjugated to polylysine.

A second embodiment of the present invention is a method of treating or preventing a bacterial infection with a porphycene compound conjugated to polylysine.

A third embodiment relates to a method of destroying or preventing bacterial populations by contacting with a porphycene compound conjugated with polylysine and irradiating with light.

These and other objects of the present invention are made possible by novel porphycenes conjugated to polylysine of formula (I)

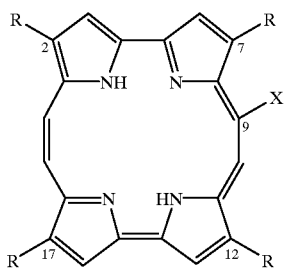

(I)

where R is a $C_{1-20}$ alkyl or $C_{1-20}$ alkoxy $C_{1-20}$ alkyl; and
X is a substituent covalently bound to the porphycene marcrocycle through an oxygen atom or a nitrogen atom, and bearing at least one carboxylic acid function through which X is conjugated to a polylysine moiety via an amide link.

BRIEF DESCRIPTION OF THE DRAWINGS

FIG. 9 is a table comparing the relative photosensitivity of *S. aureus, E. coli* and *C. albicans* and *A. laidlawii*; and FIGS. 10–11 illustrate photoinactivation with poly-lys-BOHTMPn against two mammalian cell lines (one non-transformed, namely human fibroblasts; another of malignant type, namely amelanotic melanoma).

DETAILED DESCRIPTION OF THE PREFERRED EMBODIMENTS

Figure 1:
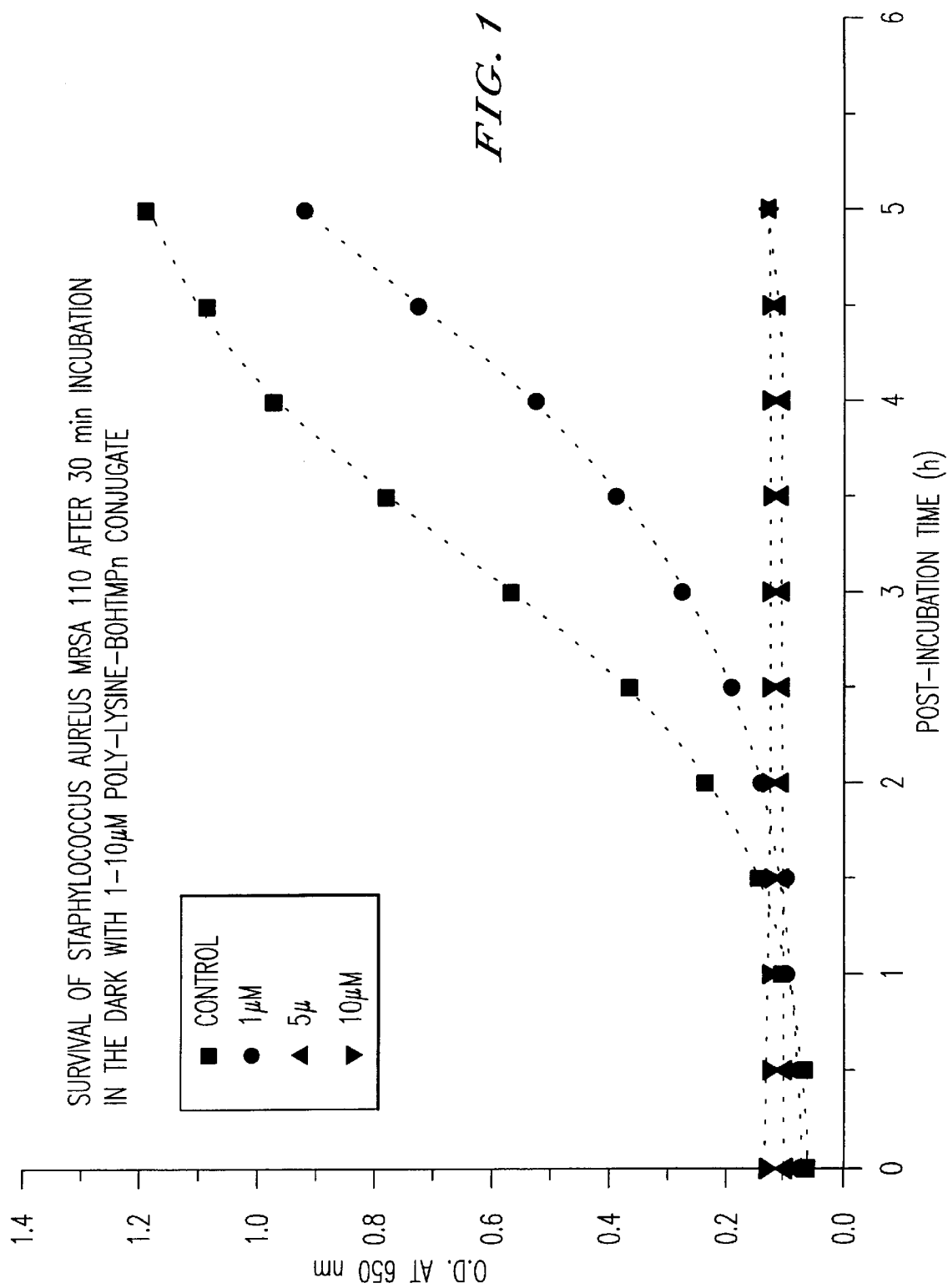
FIGS. 1–2 illustrate the toxicity to *S. aureus* of a poly-lys-BOHTMPn conjugate, in the dark.

The novel porphycene of the present invention of formula (I) bear a polylysine

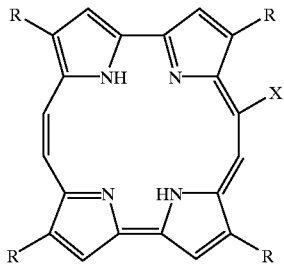

(I)

where R is a $C_{1-20}$ alkyl or $C_{1-20}$ alkoxy $C_{1-20}$ alkyl; and
X is a substituent covalently bound to the porphycene marcrocycle through an oxygen atom or a nitrogen atom, and bearing at least one carboxylic acid function through which X is conjugated to a polylysine moiety via an amide link.

In a preferred embodiment, R is a $C_{1-12}$ alkyl or $C_{1-12}$ alkoxy $C_{1-12}$ alkyl. R may be a straight or branched chain alkyl group or may have a structure $-(CH_2)_m-O-(CH_2)_n-CH_3$ where m and n are each independently an integer of from 1 to 12.

The group X may be covalently bound to the porphycene ring through an oxygen atom (e.g. ethers or esters) or a nitrogen atom (e.g amide, amines or imides) with, in all such groups one or more free carboxylic acid functions incorporated within the function X. In a preferred embodiment, the group X includes at least one carboxylic acid group and is bound to the porphycene ring through an ester or amide linkage. Non-limiting examples of the group X, as an ether group include $-O-(CH_2)_pCO_2H$, $-O-(CH_2)_rC_6H_4CO_2H$, and $-O-(CH_2)_rC_6H_3(CO_2H)_2$, where p and r are each independently an integer of from 1 to 10.

Representative X groups include $X=NHCO(CH_2)_nCO_2H$, where n=1–10 and related compounds as set forth in U.S. Pat. No. 5,610,175, incorporated by reference herein and related compounds, with conjugation via the free $CO_2H$ group and an amide link with polylysine.

Desirable cationic porphycenes are synthesized through conjugation of a porphycene bearing a free carboxylic acid function with polylysine. Preparations of the latter, of varying molecular weight are available commercially. Preparations of representative porphycene carboxylic acids have been described previously. See U.S. Pat. No. 5,610,175 incorporated herein by reference.

The porphycene compounds of the present invention may be prepared by conventional methods known to those of ordinary skill in the art.

Conjugation of a carboxylic acid containing porphycene compound with polylysine may be conducted by conventional methods known to those of ordinary skill in the art. The illustrative examples provided in this application provide further guidance.

As described herein porphycenes containing 9-ether and 9-amido substituents terminating with free carboxylic acids have been conjugated with polylysine of a molecular weight based on viscosity 1,000–4,000 or 15,000–30,000 (Yaron et al., *Biochim. Bioplhys. Acta*, 78, 397 (1963)). With the longer polymers, some toxicity to bacterial and fungal cells may be observed on a concentration dependent basis. Also, dark toxicity is influenced by porphycene structure. Similarly, dark toxicity was observed when human fibroblasts were exposed to polylysine-BOHTMPn conjugate prepared with polylysine of molecular weight 15,000–30,000. No dark toxicity was observed for polylysine-Glam TMPn conjugate using polylysine of molecular weight 1,000–4,000 for either target microorganisms or human fibroblasts or keratinocytes.

The polylysine conjugated porphycene compound of the present invention may be used in photodynamic therapy in a manner analogous to known methods of photodynamic therapy. Accordingly, it is within the level of skill of those of ordinary skill in the art of photodynamic therapy to determine effective amounts, modes of administration and activation methods, without undue experimentation.

In a preferred embodiment the polylysine conjugated porphycene compound of the present invention is administered topically.

All preparations show exceedingly strong in vitro inactivation of target microorganisms after incubation for 1–30 minutes with the polylysine-porphycene conjugates followed by exposure to white light from commercially-available light sources. Since all of these conjugate preparations are water-soluble, suitable galenical formulations for clinical use can be prepared as aerosols, sprays, solutions, gels, ointments, or creams by well-known procedures to those skilled in the art.

Figure 2:
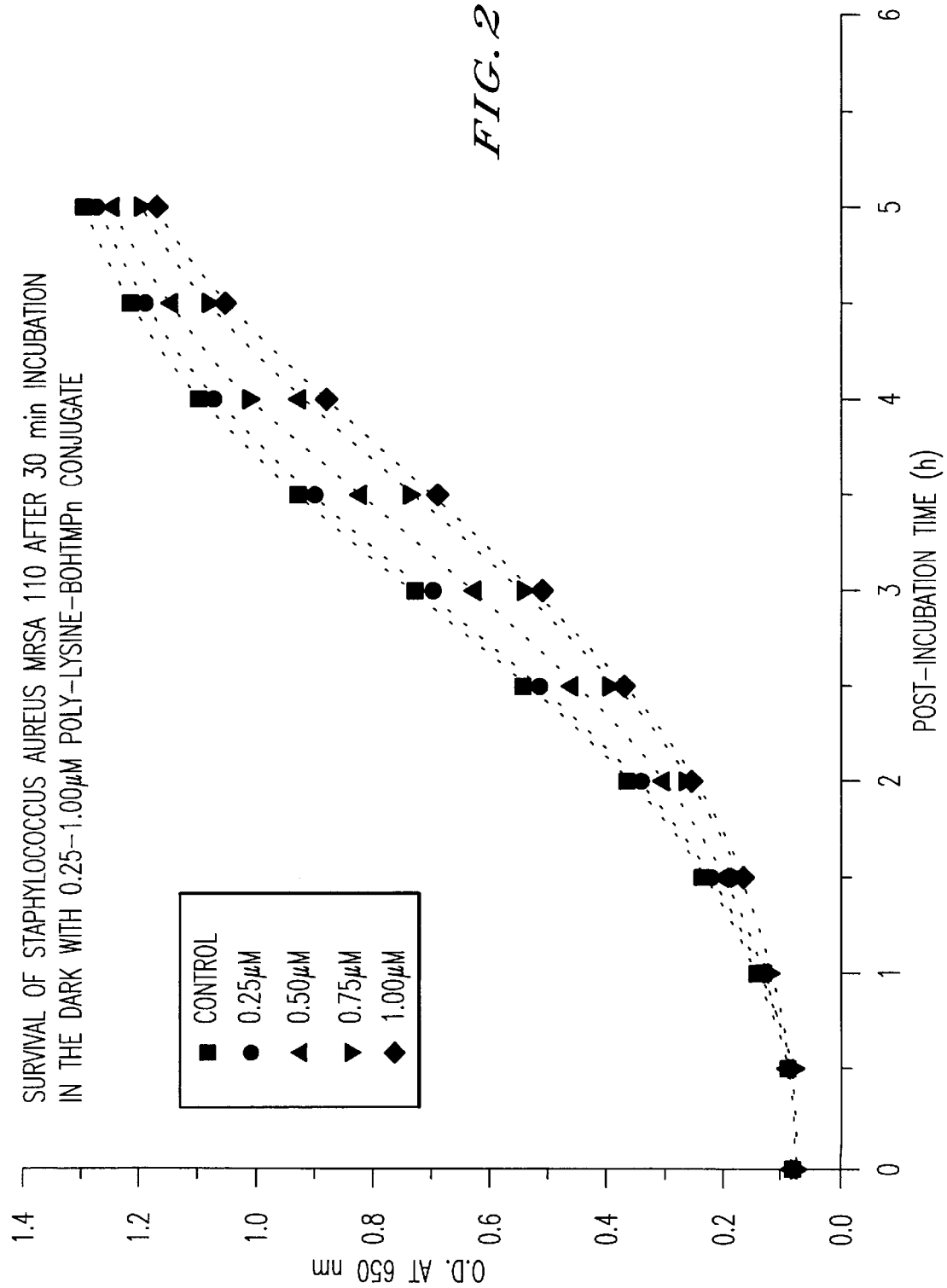

FIGS. 1–2—The poly-lys-BOHTMPn conjugate is clearly toxic to S. aureus in the dark, the toxicity being a function of the conjugate concentration. It becomes negligible only at porphycene concentrations below 0.5 μM. This is probably due to the perturbation of the native architecture of the cell membrane by the relatively long poly-lys chain.

Figure 3:
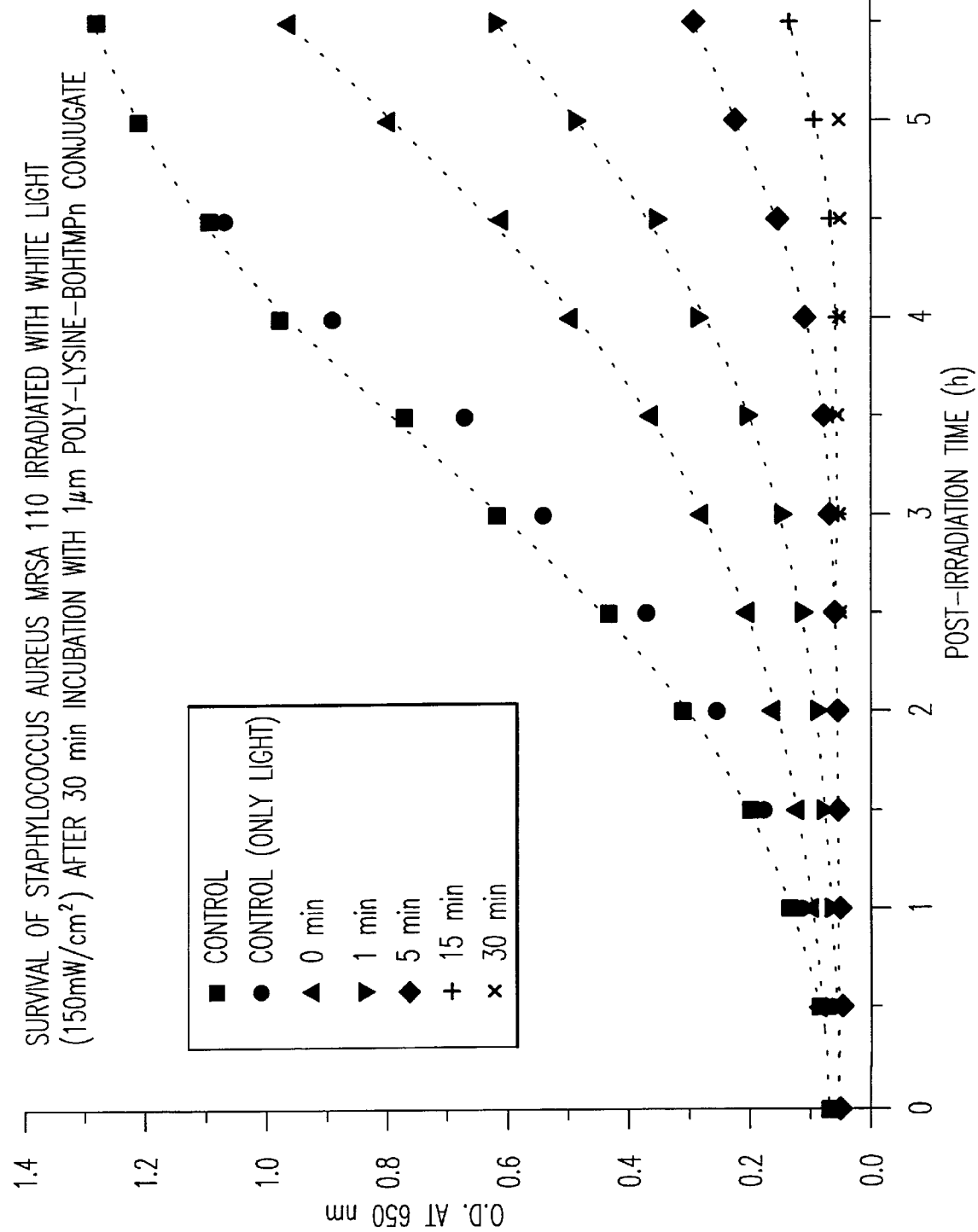
FIGS. 3–4 illustrate photoinactivation of *S. aureus* upon irradiation, with 10 µM poly-lys-BOHTMPn.
Figure 4:
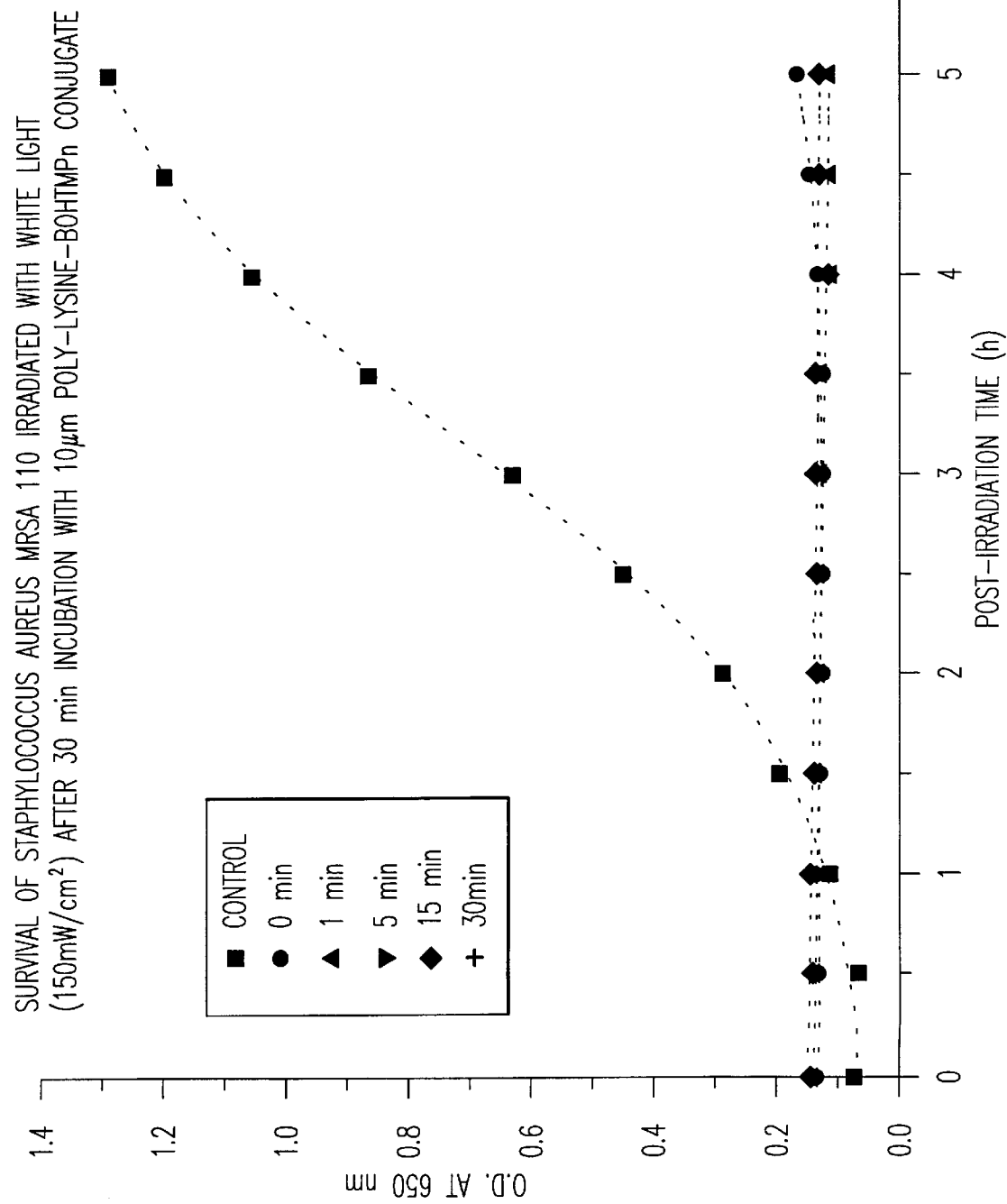

FIGS. 3–4—The complete photoinactivation of S. aureus was achieved after 1 min. irradiation with 10 μM poly-lys-BOHTMPn, whereas for 1 μM porphycene a total sterilization was achieved after 30 min. irradiation. Light alone has no effect on cell survival.

Figure 5:
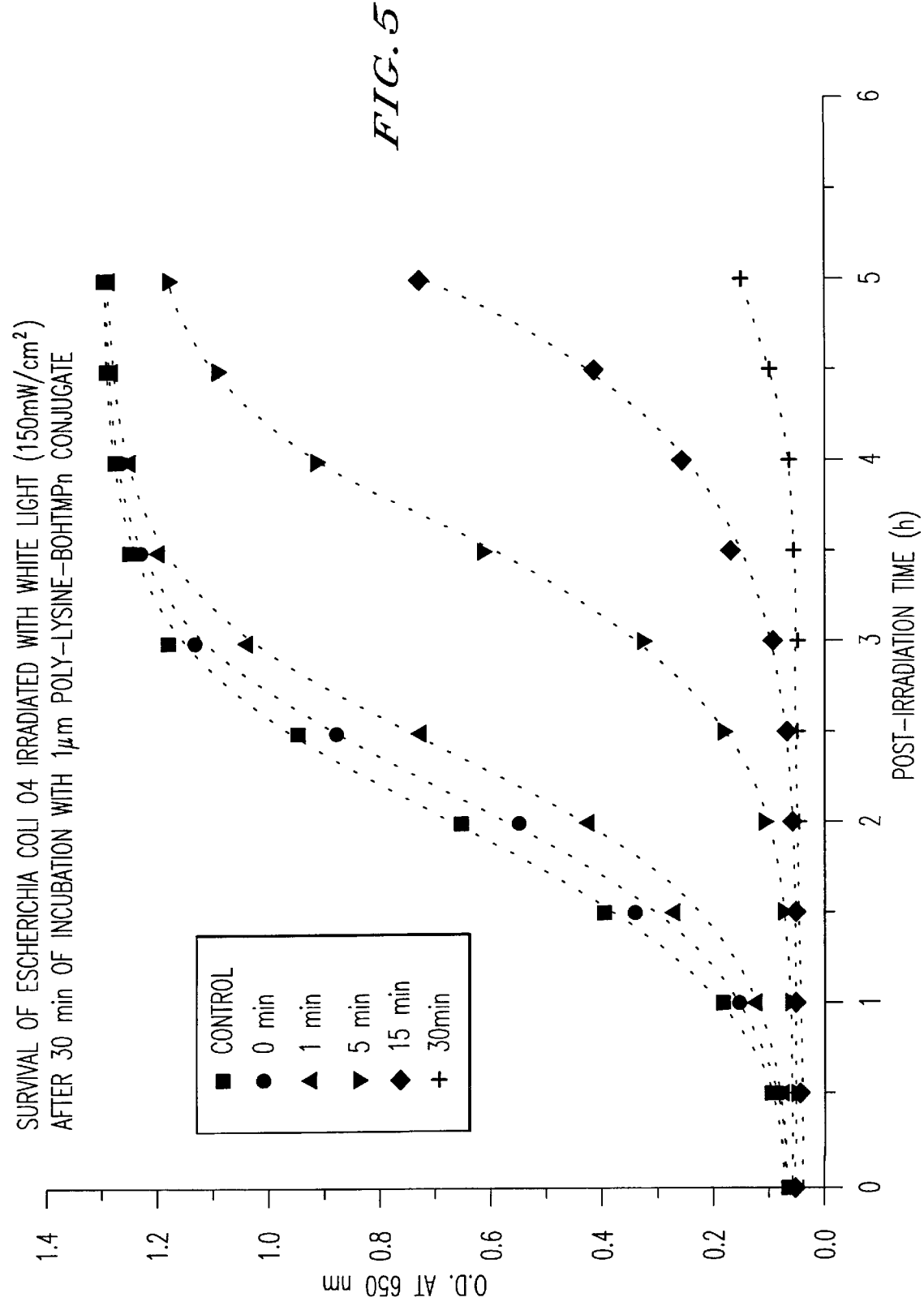
FIGS. 5–6 illustrate photoinactivation of *E-coli* upon irradiation, with1 µM poly-lys-BOHTMPn.
Figure 6:
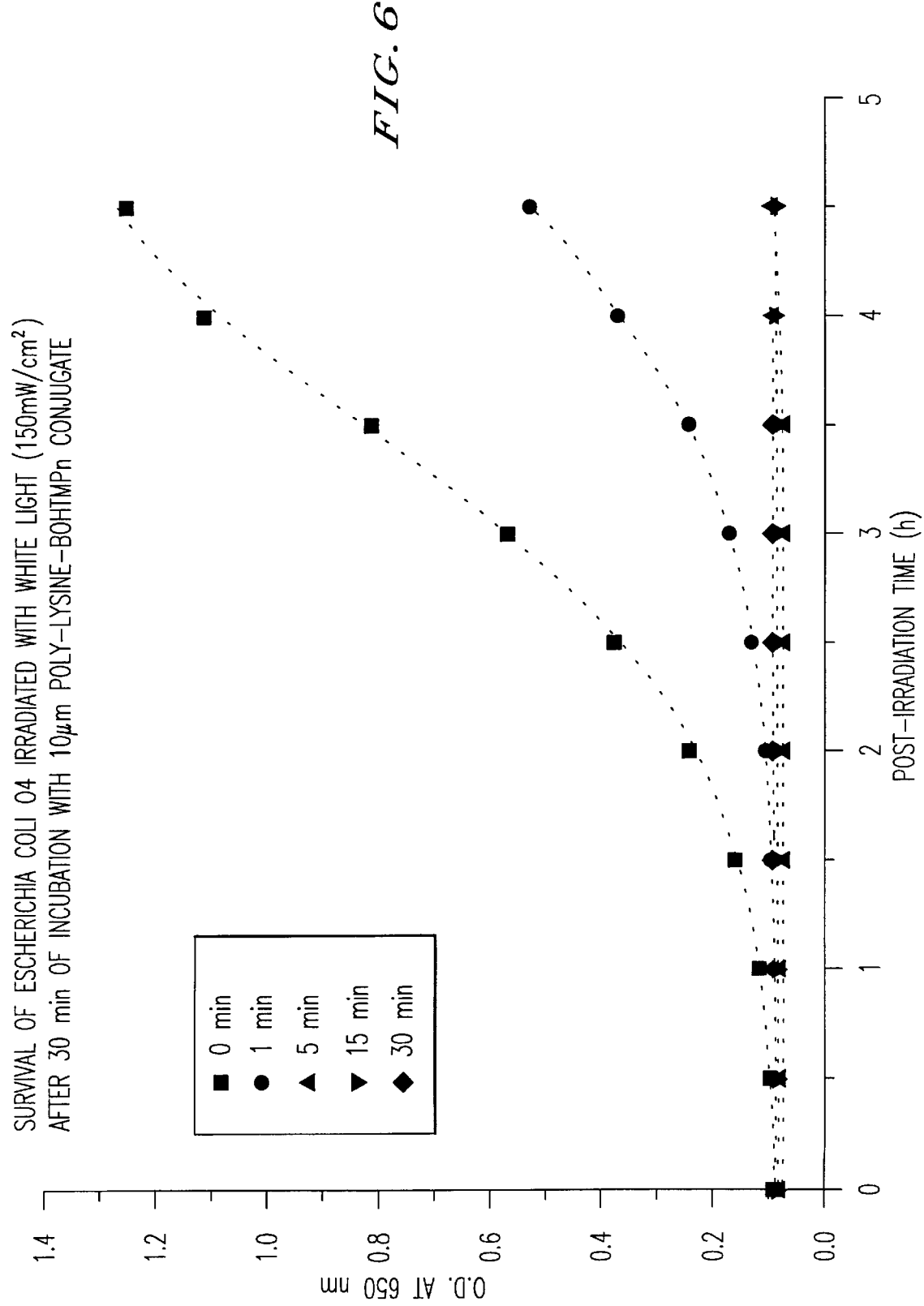

FIGS. 5–6—For E-coli, the effect of 1 μM poly-lys-BOHTMPn was almost coincidental with that observed for S. aureus (namely, total sterilization is approached after 30 min. irradiation). In the presence of 10 μM poly-lys-BOHTMPn, an extensive inactivation is observed after 1 min. irradiation and a total sterilization appears to occur after 5 min.

Figure 7:
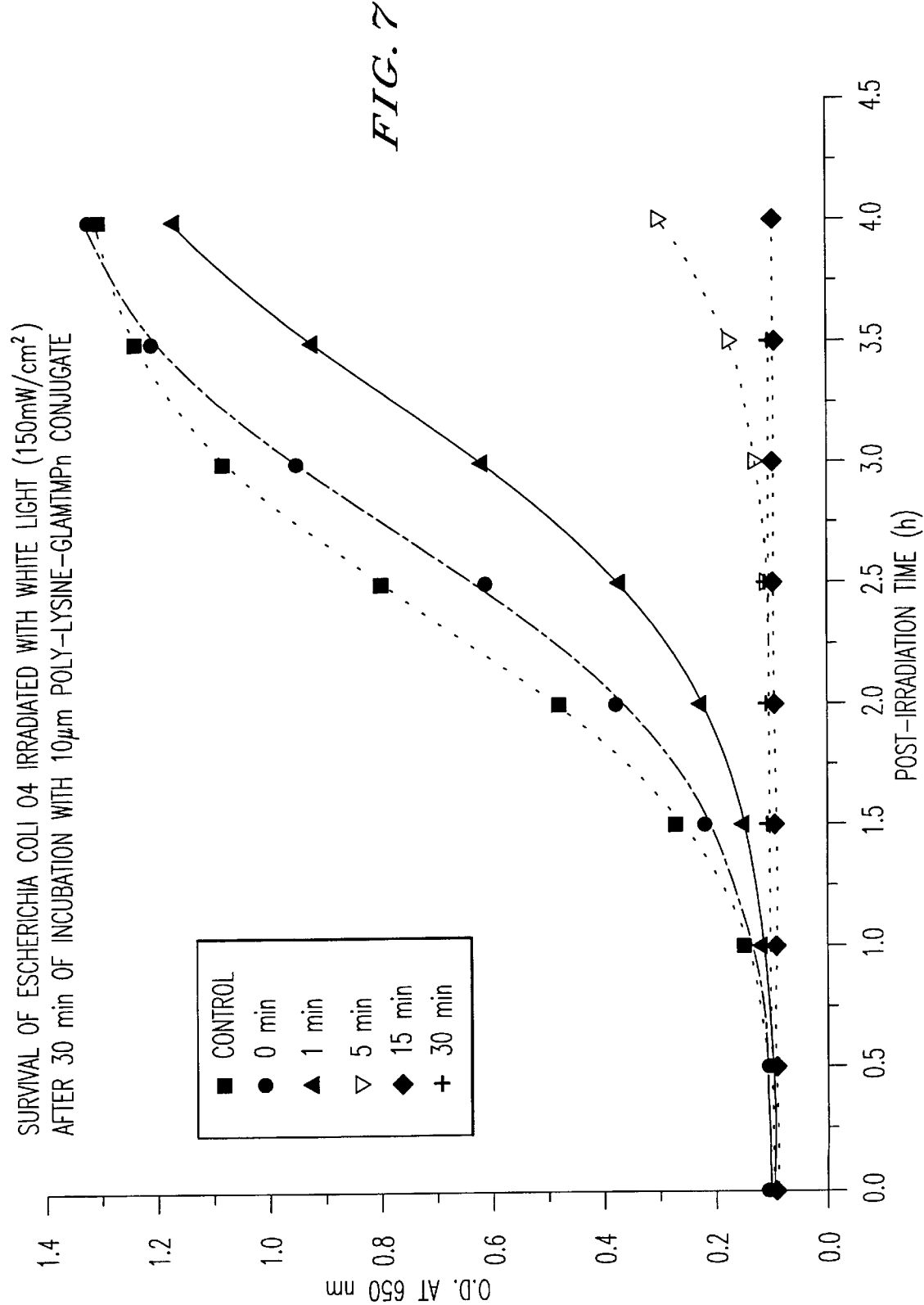
FIG. 7 illustrates photoinactivation of *E. coli* upon irradiation, with 10 µM poly-lys-Glam-TMPn.

FIG. 7—For 10 μM poly-lys-Glam-TMPn a total photoinactivation of E. coli was obtained after 15 min. irradiation; the dark toxicity of this porphycene is substantially lower than that observed for 10 μM poly-lys-BOHTMPn.

Figure 8:
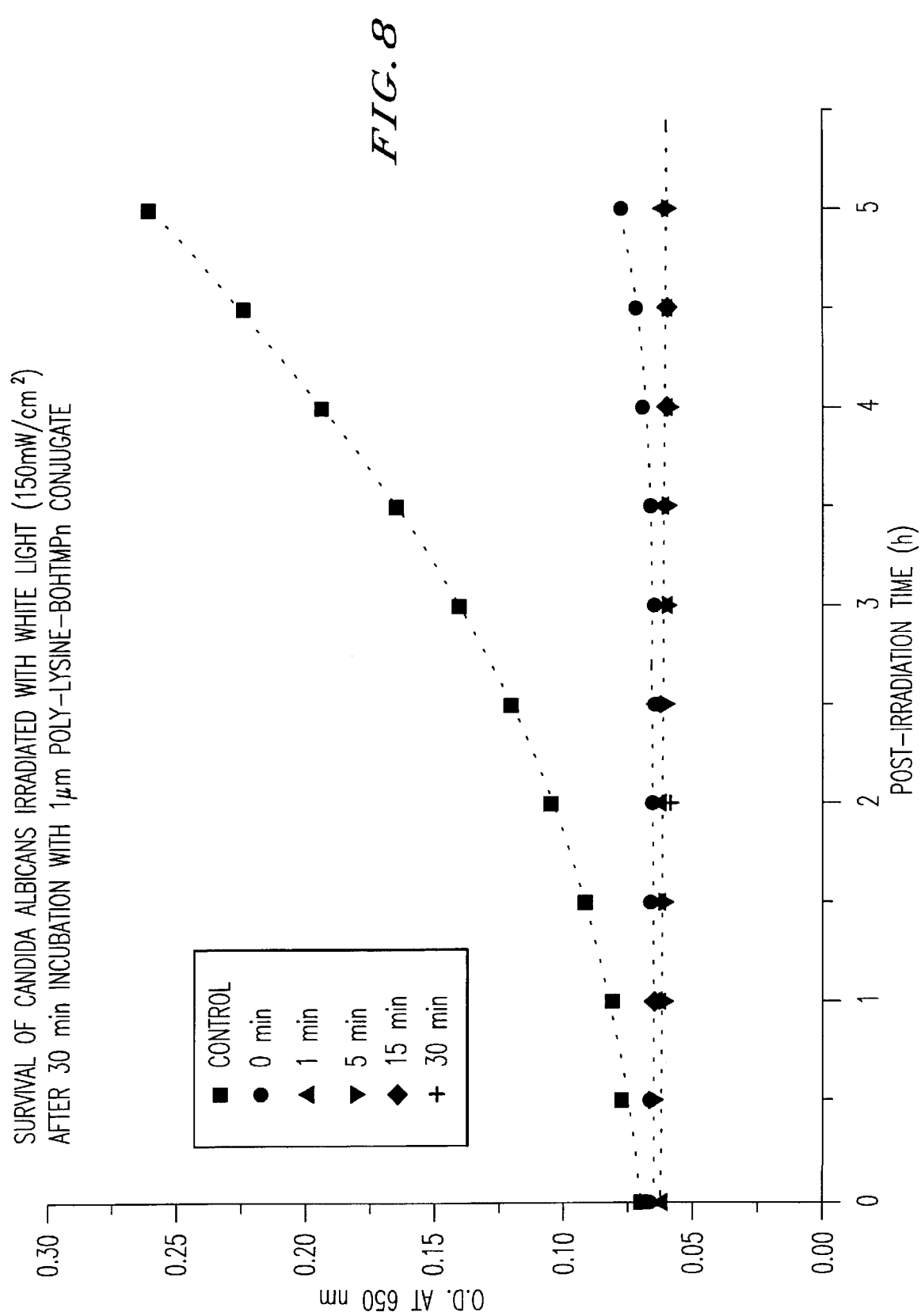
FIG. 8 illustrates photoinactivation of *C. albicans* upon irradiation, with 1 µM poly-lys-BOHTMPn.

FIG. 8—C. albicans is also very sensitive to 1 μM poly-lys-BOHTMPn, even though a high level of dark toxicity can be observed. In any case, short irradiation times are sufficient to induce a total growth inhibition.

FIG. 9—A comparative description of the relative photosensitivity of S. aureus, E. coli and C. albicans and A. laidlawii, is provided in this table; the colony-forming-unit assay allows a quantitative evaluation. Clearly, in all cases 15 min. of exposure to light induce a loss of cell survival by at least three orders of magnitude (or even higher for the bacteria). the photoinactivation efficiency is especially large for mycoplasma, where a 5-log decrease in survival was obtained after 5 min. irradiation.

FIGS. 10–11—On the basis of the above reported observations, investigation of the dark toxicity of poly-lys-BOHTMPn has been conducted against two mammalian cell lines (one non-transformed, namely human fibroblasts; another of malignant type, namely amelanotic melanoma). Experimental results indicate, some dark toxicity is observed at concentrations as low as 0.25 μM. The toxic effect appears to be due to the length of the poly-lys polymer, since when a 1,000–4,000. MW poly-lys was used there was no detectable dark toxicity against fibroblasts up to at least 5 μM concentrations.

The cationic porphycene-polylysine conjugates described herein, especially those incorporating polylysine of viscosity molecular weight 1,000–4,000 used in conjunction with light of wavelengths 330–750 mn have great utility for inactivation of undesirable and often lethal microorganisms in certain clinical situations presently of great concern to human health. Applications include the treatment of periodontal disease where flowable formulations can penetrate into crevasses harboring bacterial populations. Thermosetting gels can beneficially maintain the cationic porphycene photosensitizers in the periodontal pocket to optimize contact of the dye with the microorganisms prior to irradiation with light. Aerosol preparations and aqueous sprays of the dye conjugates can be applied post-surgically to areas of the human or animal anatomy exposed to infection by bacteria or other microorganisms which are present in hospital operating rooms. Application of visible light can be effected by the operating theater overhead lighting systems, or by an auxiliary lamp light source appropriately placed close to or within the exposed body cavity prior to wound closure. Under battlefield conditions tissues exposed to microorganisms infections can be sterilized prior to arrival of evacuation transport using aerosols, sprays, solutions, etc. of the dye photosensitizers coupled with light from a portable, rechargeable battery-powered light source. In all cases the ability to destroy populations of antibiotic-resistant bacterial populations is of special significance.

According to another embodiment of the present invention is a method of destroying or preventing bacterial populations by irradiating a surface, having thereon, a conjugated porphycene compound as claimed. More specifically, sterilization may be performed by immersing an article to be sterilized in a solution of conjugated porphycene compound, concurrently or sequentially irradiating with a white light source, such as a sodium or halogen lamp, or fluorescent tube light source. Immersion and irradiation are conducted for a time sufficient to effect sterilization, the adjustment of each parameter being within the level of skill of those of ordinary skill in the art, taking into consideration, the solution concentration, and light intensity. The article, in need of sterilization may be a surgical instrument or prosthetic device. Alternatively, the article in need of sterilization, may be coated with the conjugated porphycene compound (such as by incorporation of the porphycene within a paint composition), then irradiated with light for a time and intensity sufficient to affect sterilization. The effective concentration of conjugated porphycene compound within a sterilizing solution or sterilizing coating may be determined by routine experimentation, by those of ordinary skill in the art. Suitable carriers for sterilizing solutions (e.g. solvents) and sterilizing coatings (e.g. vehicles) may be selected by those of ordinary skill in the art without undue experimentation.

Having generally described this invention, a further understanding can be obtained by reference to certain specific examples which are provided herein for purposes of illustration only and are not intended to be limiting unless otherwise specified.

EXAMPLES

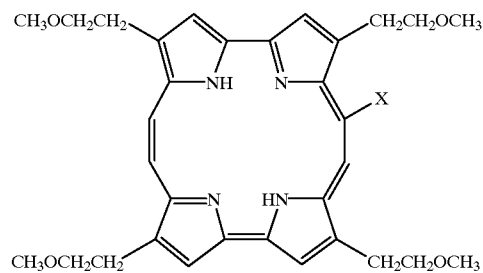

Glam TMPn
X = NHCO(CH$_2$)$_3$CO-(poly lysine)

BOHTMPn
X = p-OCH$_2$C$_6$H$_4$CO-(poly lysine)

2,7,12,17-Tetrakis(2-methoxyethyl)-9-Glutaramidoporphycene-N$_8$-Poly-L-Lysine Hydrochloride (GlamTMPn-Polylysine-HCl)

6.7 mg of 2,7,12,17-Tetrakis(2-methoxyethyl)-9-glutaramido-porphycene (GlamTMPn), 50 mg of 1-ethyl-3-(3-dimethylaminopropyl)carbodiimide hydrochloride (EDAC HCl), and 50 mg of poly-L-lysine hydrochloride (Sigma 7890) were dissolved at 0° C. in an amine-free solvent mixture of 4 ml of pyridine, 4 ml of dimethylformamide (DMF), and 2 ml of deionized water. The blue solution was stirred for 2 h at 0° C., for an additional 48 h at room temperature, and then added to ca. 12–15 g of silica gel (Merck, Silica gel 60, 63–200 µm). The coupling reaction was monitored by thin-layer chromatography (TLC, silica gel, dichloromethane/methanol/ethyl acetate 1/1/1). The blue wet silica gel was loaded onto a 12×4 cm chromatography column of silica gel 60 (63–200 µm; solvent as for TLC). Chromatography first removed unreacted less polar porphycene starting material and/or by-products in the form of a small blue fraction. Chromatography was continued by consecutive elution with neat methanol (ca. 96%, Merck), methanol/deionized water 1/1, and neat water. To remove the colorless, water-soluble 1-ethyl-3-(3-dimethylaminopropyl)urea (EDU, reaction product of EDAC), 0.37% aqueous hydrochloric acid (1 ml of conc. HCl in 100 ml of water) was then used as an eluent. The blue remaining porphycene-polylysine fraction was eluted finally after addition of methanol to the dilute hydrochloric acid (1/1). the resulting fraction, a blue solution, was concentrated to a few milliliters under reduced pressure (10–16 torr) at a temperature of max. 35° C. After 24–48 h of freeze drying ($10^{-3}$ torr, $-15°$ C.), the dark blue residue precipitated during a period of 4–8 h under reduced pressure at room temperature ($10^{-3}$ torr, 20° C.). Yield: 20 mg.

2,7,12,17-Tetrakis(2-methoxyethyl)-9-p-Carbamidobenzyloxyporphycene-$N_8$-Poly-L-Lysine Hydrochloride (BOHTMPn-Polylysine-HCl)

6.8 mg of 2,7,12,17-tetrakis(2-methoxyethyl)-9-p-carboxybenzyloxy-porphycene (BOHTMPn), 50 mg of 1-ethyl-3-(3-dimethylaminopropyl)carbodiimide hydrochloride (EDAC-HCl), and 50 mg of poly-L-lysine hydrochloride (Sigma 7890) were dissolved at 0° C. in an amine-free solvent mixture of 4 ml of pyridine, 4 ml of dimethylformamide (DMF), and 2 ml of deionized water. The blue solution was stirred first for 2 h at 0° C., then for 48 h at room temperature. The coupling reaction was carried by addition of ca. 12–15 g of silica gel (Merck, Silica gel 60, 63–200 µm) and monitored by thin-layer chromatography (TLC, silica gel, dichloromethane/methanol/ethyl acetate 1/1/1). The blue wet silica gel was loaded onto a 12×4 cm chromatography column of silica gel 60 (63–200 µm; solvent as for TLC). Chromatography first removed unreacted less polar porphycene starting material and/or by-products in the form of small blue fraction. Chromatography was continued by consecutive elution with neat methanol (ca. 96%, Merck), methanol/dionized water 1/1, and neat water. To remove the colorless, water-soluble 1-ethyl-3-(3-dimethylaminopropyl)urea (EDU, reaction product of EDAC), 0.37% aqueous hydrochloric acid (1 ml of conc. HCl in 100 ml of water) was then used as an eluent. The blue remaining porphycene-polylysine fraction was eluted finally after addition of methanol to the dilute hydrochloric acid (1/1). The resulting fraction, a blue solution, was concentrated to a few milliliters under reduced pressure (10–16 torr) at a temperature of max. 35° C. After 24–28 h of freeze drying ($10^{-3}$ torr, $-15°$ C., the blue residue precipitated during a period of 4–8 h under reduced pressure at room temperature ($10^{-3}$ torr, 20° C.). Yield: 22 mg.

Photoantimicrobial Activity of Polylysine-Porphycene Conjugates

Two covalent conjugates between polylysine (MW 15,000–30,000) and two porphycene derivatives [9-(Glutaric acid amido)-2,7,12,17-tetrakis(methoxyethyl) porphycene, GlamTMPn; and 9-(p-Benzyloxy carboxylic acid)-2,7,12,17-tetrakis(methoxyethyl)porphycene, BOHTMPn] were prepared by chemical synthesis, as discussed above.

The phototoxic activity of such derivatives was tested against selected microbial strains with an aim to define the spectrum of activity against Gram-positive bacteria (*Staphylococcus aureus*)

Gram-negative bacteria (*Escherichia coli*)

Yeasts (*Candida albicans*)

Mycoplasma (*Acholeplasma laidlawii*)

The experimental protocols for phototoxicity studies in all cases were as follows:

porphycene concentration: 1–10 µm dark incubation time prior to irradiation: 30 min.

microbial cells: $10^8$–$10^9$ cells/ml ($10^7$ for *C. albicans*)

irradiation medium: phosphate-buffered saline, pH 7.4 light source: quartz/halogen lamp with white light emission irradiation fluence rate: 15 mW/cm$^2$ irradiation time: 1–30 min.

The response of the microbial cells to porphycene photosensitization was assessed by two independent methods:

(1) The rate of cell growth as a function of post-irradiation time, which is measured by following the time-dependent increase in optical density of cell suspensions;

(2) The colony-forming-units (cfu) counted at 24 h (48 h for *C. albicans*) after the end of irradiation, which give a more quantitative evaluation of the microbial cell photoinactivation.

The results obtained are shown in FIGS. 1–9 hereto. As clearly shown therein, the porphycenes of this invention, conjugated through a carboxylic acid bearing moiety to a polylysine, meets the above criteria for effective photoactive anti-microbial agents. These cationic porphycenes are isolated as hydrochloride salts, but may be used in any orally, topically or surface acceptable form, including the cationic preparation as a liquid/aerosol, pharmaceutically acceptable salts, and the like.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A porphycene compound, comprising a porphycene in conjugation with polylysine.

2. The porphycene compound of claim 1 wherein said polylysine has a viscosity molecular weight of 500–30,000.

3. The porphycene compound of claim 1 wherein said polylysine has a viscosity molecular weight preferably 1,000–10,000.

4. The porphycene compound of claim 1 wherein said polylysine has a viscosity molecular weight of 1,00 to 4,000.

5. The porphycene compound of claim 1, wherein said porphycene is of formula I,

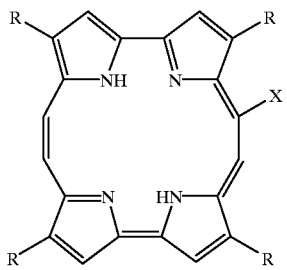

(I)

where R is a $C_{1-20}$ alkyl or $C_{1-20}$ alkoxy $C_{1-20}$ alkyl; and

X is a substituent covalently bound to the porphycene marcrocycle through an oxygen atom or a nitrogen atom, and bearing at least one carboxylic acid function through which X is conjugated to a polylysine moiety via an amide link.

6. The porphycene compound of claim 5, 9-(glutaric acid amide)-2,7,12,17-tetrakis(methoxyethyl) porphycene conjugated with polylysine of molecular weight 1,000–4,000.

7. The porphycene compound of claim 5, 9-(p-benzyloxy carboxylic acid)-2,7,12,17-tetrakis (methoxyethyl) porphycene conjugated with polylysine of molecular weight 1,000–4,000.

8. The porphycene compound of claim 5, wherein X=NHCO(CH$_2$)$_n$CO$_2$H, where n=1–10, X=OCH$_2$C$_6$H$_4$CO$_2$H or X=OCH$_2$C$_6$H$_3$(CO$_2$H)$_2$.

9. The porphycene compound of claim 5, where R is n-propyl and X is a substituent bearing one or more carboxylic acid functions with conjugation via a free carboxylic acid group and an amide link with polylysine.

10. The porphycene compound of claim 1, 9-glutaric acid amide 2, 7, 12 17 tetra-n-$C_{1-20}$ alkyl porphycene conjugated with polylysinc of molecular weight 1,000 to 4,000.

11. A method of inactivating a microbial population by contacting the microbial population with the porphycene compound of claim 1 and irradiating with white light or light in the wavelength 330–750 nm, with a total light dose below the threshold needed to cause photodynamic effects on host mammalian cells.

12. The method of claim 11, wherein said wavelength of light is in the range of 570–750nm.

13. The method of claim 11 where said porphycene compound is administered in aerosol, spray solution, or liquid gel formulation to a living mammal bearing an undesirable microbial population followed by radiation with light from sources of white light, with or without filters.

14. A sterilizing composition comprising:
a) the porphycene compound of claim 1; and
b) a carrier.

15. The sterilizing composition of claim 14, wherein said composition is a solution and said carrier is a solvent for said porphycene.

16. The sterilizing composition of claim 14, wherein said composition is a coating composition.

17. A method of sterilizing an article comprising:
a) contacting an article with the porphycene compound of claim 1; and
b) irradiating said article and porphycene compound with light, for an amount and time sufficient to affect sterilization.

18. The method of claim 17, wherein contacting of said article is by immersion in a solution of said porphycene compound.

19. The method of claim 17, where contacting of said article is by coating said article with a coating composition comprising said porphycene compound.

* * * * *

UNITED STATES PATENT AND TRADEMARK OFFICE
CERTIFICATE OF CORRECTION

PATENT NO. : 6,107,326  
DATED : August 22, 2000  
INVENTOR(S) : Giulio Jori

Page 1 of 1

It is certified that error appears in the above-identified patent and that said Letters Patent is hereby corrected as shown below:

Title page,  
Title, "PORPHYCENES", should read, -- NOVEL PORPHYCENES --.

Drawings,  
Figure 3, "(150 mW/cm$^2$)", should read -- (15 mW/cm$^2$) --.  
Figure 4, "(150 mW/cm$^2$)", should read -- (15 mW/cm$^2$) --.  
Figure 5, "(150 mW/cm$^2$)", should read -- (15 mW/cm$^2$) --.  
Figure 6, "(150 mW/cm$^2$)", should read -- (15 mW/cm$^2$) --.  
Figure 7, "(150 mW/cm$^2$)", should read -- (15 mW/cm$^2$) --.  
Figure 8, "(150 mW/cm$^2$)", should read -- (15 mW/cm$^2$) --.  
Figure 9, "(150 mW/cm$^2$)", should read -- (15 mW/cm$^2$) --.

Signed and Sealed this

Sixteenth Day of April, 2002

Attest:

JAMES E. ROGAN  
*Director of the United States Patent and Trademark Office*

*Attesting Officer*